US005753487A

United States Patent [19]

Eigtved et al.

[11] Patent Number: 5,753,487
[45] Date of Patent: May 19, 1998

[54] STABILISED PHENYLALANINE AMMONIA LYASE

[75] Inventors: Peter Eigtved, Holte; Ib Groth Clausen, Hillerød, both of Denmark

[73] Assignee: Novo Nordisk A/S, Bagsvaerd, Denmark

[21] Appl. No.: 556,963

[22] PCT Filed: Jun. 9, 1994

[86] PCT No.: PCT/DK94/00224

§ 371 Date: Dec. 12, 1995

§ 102(e) Date: Dec. 12, 1995

[87] PCT Pub. No.: WO95/00171

PCT Pub. Date: Jan. 5, 1995

[51] Int. Cl.[6] .................... C12N 9/88; A61K 38/51; C07K 1/00; C07H 21/04
[52] U.S. Cl. .................. 435/232; 424/94.5; 435/172.1; 435/172.3; 435/252.3; 435/254.11; 435/254.2; 435/254.21; 435/254.23; 435/254.3; 435/254.6; 435/320.1; 530/402; 536/23.2; 935/22
[58] Field of Search .................. 435/188, 172.1, 435/320.1, 69.1, 252.3, 232, 254.11, 254.2, 254.21, 254.23, 254.3, 254.6, 172.3; 536/23.2; 530/402; 935/22

[56] References Cited

U.S. PATENT DOCUMENTS 4,762,707  8/1988  Jansen ..................... 424/180.1
4,970,156  11/1990  Avrameas et al. ............. 435/174

OTHER PUBLICATIONS

Haskins (1981) "Enzymatic control of Dietary Substrate intake", pp. 185–197, *Advances in the Treatment of Inborn Errors of Metabolism*(Crawford et al, eds), John Wiley & Sons.
Evans et al (1987) J. Indust. Micro. 2:53–58 "Effect of glycerol, polyethylene glycol and glutaraldehyde on stability of . . . ".
Gilbert et al (1981), Biochem J 199:715–723 "The effect of proteinases on phenylalanine ammonia–lyase from the yeast . . . ".
Itoh et al (1988), J gen virol 69:2907–2911, "Single Amino acid change at the fusion protein is responsible for both . . . ".
Chemical Abstracts, vol. 92, No. 1, The Abstract No. 2439y, p. 249, 1980.
Chemical Abstracts, vol. 94, No. 7, The Abstract No. 43310j, p. 226, 1981.
Chemical Abstracts, vol. 89, No. 23, The Abstract No. 191071u, p. 53–54, 1978.
National Library of Medicine, accession No. 87000699, (1986).
Patent Abstracts of Japan, vol. 9, No. 324, No. 60–155125, (1985).
National Library of Medicine, accession No. 86025495, (1985).
National Library of Medicine, accession No. 87100106, (1986).
National Library of Medicine, accession No. 89375668, (1989).

*Primary Examiner*—Robert A. Wax
*Assistant Examiner*—Einar Stole
*Attorney, Agent, or Firm*—Steve T. Zelson, Esq.; Cheryl T. Agris, Esq.

[57] ABSTRACT

This invention relates to stabilization of phenylalanine ammonia lyase against proteolytic degradation by chemical modification with crosslinking agents, or by genetic modification, a phenylalanine ammonia lyase variant, a method of preparing the variant and a pharmaceutical composition containing phenylalanine ammonia lyase.

44 Claims, No Drawings

STABILISED PHENYLALANINE AMMONIA LYASE

CROSS-REFERENCE TO RELATED APPLICATIONS

This application is a PCT/DK94/00224 filed Jun. 9, 1994, which is incorporated herein by reference.

FIELD OF INVENTION

The present invention relates to a stabilised phenylalanine ammonia lyase, a phenylalanine ammonia lyase variant, a method of preparing the variant and a pharmaceutical composition containing phenylalanine ammonia lyase.

BACKGROUND OF THE INVENTION

Hyperphenylalaninemia, which may be defined as a plasma level of phenylalanine of more than 120 µmol/l, is a hereditary disease caused by a deficiency in the hepatic enzyme phenylalanine hydroxylase or (in rare cases) its cofactor tetrahydropterin or the cofactor-regenerating enzyme dihydropterin reductase. The disease exists in different forms, phenylketonuria (PKU) which, if the patient is on a normal diet, has plasma phenylalanine levels of more than 1200 µmol/l, and non-PKU hyperphenylalaninemia which has lower levels of plasma phenylalanine.

In normal subjects, phenylalanine hydroxylase converts phenylalanine to tyrosine. Highly increased plasma levels of phenylalanine (>600 µmol/L) result in mental retardation. The effect appears to be ascribable to phenylalanine itself (not any metabolites thereof), but the mechanism is not yet fully understood. In most industrialised countries, newborn children are routinely screened for hyperphenylalaninemia. The negative effects of increased plasma levels of phenylalanine may, to a large extent, be prevented if a low-phenylalanine diet is introduced shortly after birth and continued well into adolescence. The aim is to obtain plasma phenylalanine levels of 180–425 µmol/l. After adolescence, the low-phenylalanine regimen may be somewhat relaxed, although phenylalanine-free products are still a significant component of the diet. Pregnant hyperphenylalaninemic patients are required to go back on a strict low-phenylalanine diet in order to avoid the effects of excessive intrauterine phenylalanine, i.e. congenital malformation, microcephaly and mental retardation of the fetus.

The strict low-phenylalanine regimen is tiresome for the patients and their families, and is very difficult to enforce beyond childhood. Enzyme therapy to make up for the phenylalanine hydroxylase deficiency would therefore provide a great improvement in the treatment of hyperphenylalaninemia. Unlike phenylalanine hydroxylase, another phenylalaninedegrading enzyme, phenylalanine ammonia lyase, requires no cofactors to be active. Phenylalanine ammonia lyase converts phenylalanine to trans-cinnamic acid which, via coenzyme A, is converted to benzoic acid which reacts with glycine and is then excreted via urine primarily as hippurate. The enzyme may, for instance, be obtained from the yeast *Rhodotorula glutinis* (also known as *Rhodosioridium toruloides*). It has previously been suggested to use phenylalanine ammonia lyase for treatment of hyperphenylalaninemia, vide for instance, J. A. Hoskins et al., Lancet, Feb. 23, 1980, pp. 392–394. Proteolytic degradation of the enzyme in the gastrointestinal tract has been recognized, e.g. by H. J. Gilbert and G. W. Jack, *Biochem. J.* 199, 1981, pp. 715–723. Various attempts to overcome this problem have been published. Thus, L. Bourget and T. M. S. Chang, *Biochim. Biophys. Acta* 883, 1986, pp. 432–438, propose microencapsulation of the enzyme in "artificial cells" composed of phenylalanine ammonia lyase mixed with hemoglobin and enclosed in microspheres covered by a cellulose nitrate membrane. H. J. Gilbert and M. Tully, *Biochem. Biophys. Res. Comm.* 131(2), 1985, pp. 557–563 propose using permeabilised cells of *Rhodosporidium toruloides* containing the enzyme. However, both of these approaches may have drawbacks such as low specific phenylalanine ammonia lyase activity of the final preparation or high cost due to processing or formulation.

DESCRIPTION OF THE INVENTION

The object of the present invention is to overcome the drawbacks of the previously suggested methods of stabilising phenylalanine ammonia lyase.

Accordingly, the present invention relates to an enzyme preparation comprising phenylalanine ammonia lyase (PAL) stabilised against proteolytic degradation by chemical or genetic modification.

In a preferred embodiment of the enzyme preparation of the invention, the PAL is chemically stabilised by treatment with a cross-linking agent. For the present purpose, it is assumed that the cross-linking agent reinforces the conformation of PAL and makes it less accessible to proteolytic enzymes in the gastrointestinal tract by reticulating the molecule (intramolecular cross-links) to form a brace. Intermolecular cross-linking to another molecule (typically another protein) may also be advantageous to form a conjugate in which the enzyme is protected from the action of proteases. A further description of chemical cross-linking of proteins may be found in, e.g., S. S. Wong and L.-J. C. Wong, *Enzyme Microb. Technol.* 14, 1992, pp. 866–873. Preferred cross-linking reagents are selected from aldehydes, isocyanates, isothiocyanates, anhydrides and azides. Particularly preferred cross-linking agents are bifunctional reagents, i.e. compounds with two reactive groups. Examples of such reagents are pharmaceutically acceptable carbodiimides, isoxazolium derivatives, chloroformates, carbonyldiimidazole, bis-imidoesters, bis-succinimidyl derivatives, di-isocyanates, di-isothiocyanates, disylfonyl halides, bis-nitrophenyl esters, dialdehydes, diacylazides, bis-maleimides, bis-haloacetyl derivatives, di-alkyl halides and bis-oxiranes. A currently preferred cross-linking agent for the present purpose is glutaraldehyde. This compound is inexpensive, readily available and approved for a number of food-related enzyme applications. It yields a product with good mechanical properties and good recovery of the enzymatic activity.

The PAL is an intracellular enzyme and may as such be present in whole cells or permeabilised cells, or it may be present in a cell homogenate. The PAL may also be cell-free, affording a preparation which is not diluted with enzymatically inactive cell material and consequently is enriched in enzymatic activity. In the enzyme preparation of the invention, PAL preferably constitutes at least 25%, in particular at least 50%, of the enzyme protein in the preparation. In a specific embodiment, the PAL is in crystalline (i.e. substantially pure) form which may be advantageous for formulation, dosage or approval purposes.

The cross-linking reaction may be carried out at room temperature or at lower temperatures. Higher reaction temperatures during cross-linking may inactivate the enzyme. For effective cross-linking, the reaction time may vary from a few minutes to several hours. The pH of the cross-linking medium should be one which ensures reactivity of the cross-linking agent concomitantly with enzyme activity. When glutaraldehyde is used as the cross-linking agent, a pH of about 6-10 will be the most appropriate. In case of cell-free or crystalline PAL, it may be advantageous to include an auxiliary substance such as a polyamine in the cross-linking reaction.

In another aspect, the present invention relates to a PAL variant stabilised against proteolytic degradation, wherein one or more amino acid residues susceptible to proteolytic cleavage are substituted by one or more amino acid residues less susceptible to proteolytic cleavage.

In the present description and claims, the following abbreviations are used:

Amino Acids

A=Ala=Alanine
V=Val=Valine
L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Asn=Asparagine
Q=Gln=Glutamine
D=Asp=Aspartic Acid
E=Glu=Glutamic Acid
K=Lys=Lysine
R=Arg=Arginine
H=His=Histidine In describing PAL variants according to the invention, the following nomenclature is used for ease of reference: Original amino acid(s) position(s) substituted amino acid(s)

According to this nomenclature, for instance the substitution of alanine for phenylalanine in position 629 is shown as:

F629A

According to the invention, it has been found that the amino acid residues Phe, Tyr, Trp, Lys and Arg are particularly sensitive to cleavage by the major proteolytic enzymes in the gastrointestinal tract, i.e. chymotrypsin (cleavage at Phe, Tyr and Trp) and trypsin (cleavage at Lys and Arg). To improve the stability of PAL in the gastrointestinal tract, one or more of these amino acid residues may therefore be replaced by other residues which are more resistant to proteolytic cleavage.

The parent PAL may be derivable from a microorganism, in particular a fungus such as a Rhodotorula sp., Rhodosoridium sp., Sporobolus sp., Geotrichum sp., Moniliella sp., Pellicularia sp., Gonatobotryum sp., Syncerhalastrum sp., Endomyces sp., Aspergillus sp., Saccharomvcopsis sp., Eurotium sp., Glomerella sp., Cladosporium sp. or Trichosporon sp., or from a plant such as Pisum sativum, potato, sweet potato or soy bean. A particularly preferred PAL is one derivable from a strain of *Rhodosporidium toruloides* (syn. *Rhodotorula glutinis*), or a suitable homologue thereof.

In the present context, the term "homologue" is intended to indicate a PAL of which the amino acid sequence is at least 45% identical to that of the *Rhodosporidium toruloides* PAL. Sequence comparisons may be performed via known algorithms, such as the one described by Lipman and Pearson, *Science* 227, 1985, p. 1435. Sequences may be obtained from databases containing Published Sequences. Examples of homologues are PALs derivable from *Rhodotorula rubra, Lycopersicon esculentum, Nicotiana tabacum, Ipomoea batatas, Phaseolus vulgaris, Medicago sativa, Petroselinum crispum, Oryza sativa* and soybean.

In particular, the protease-stability of PAL may be improved by substituting one or more amino acid residues in the region from amino acid 629 to 674 of the PAL derivable from *Rhodosporidium toruloides*. Without wishing to be limited to any theory, it is currently assumed that this region forms a loop on the surface of the enzyme, so that the protease-sensitive amino acid residues present in this region are particularly exposed to proteolytic enzymes in the gastrointestinal tract. It is anticipated that amino acid residues in corresponding positions of homologous PALs may likewise be substituted.

More specifically, one or more amino acid residues may be substituted as follows F629A,S,V,L,E,P,N,I,Q,T,M,G,H,D
F631A,S,V,L,E,P,N,I,Q,T,M,G,H,D
W653A,S,V,L,E,P,N,I,Q,T,M,G,H,D
K654A,S,V,L,E,P,N,I,Q,T,M,G,H,D
R667A,S,V,L,E,P,N,I,Q,T,M,G,H,D
R670A,S,V,L,E,P,N,I,Q,T,M,G,H,D
F673A,S,V,L,E,P,N,I,Q,T,M,G,H,D
W674A,S,V,L,E,P,N,I,Q,T,M,G,H,D Cloning a DNA Sequence Encoding a PAL The DNA sequence encoding a parent PAL may be isolated from any cell or microorganism producing the PAL in question by various methods, well known in the art. Firstly, a genomic DNA and/or cDNA library should be constructed using chromosomal DNA or messenger RNA from the organism that produces the PAL to be studied. Then, if the amino acid sequence of the PAL is known, homologous, labelled oligonucleotide probes may be synthesized and used to identify PAL-encoding clones from a genomic library of bacterial DNA, or from a fungal cDNA library. Alternatively, a labelled oligonucleotide probe containing sequences homologous to PAL from another strain of bacteria or fungus could be used as a probe to identify PAL-encoding clones, using hybridization and washing conditions of lower stringency.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487–491.

Site-directed Mutagenesis of the PAL-encoding Sequence

Once a PAL-encoding DNA sequence has been isolated, and desirable site for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the PAL-encoding sequence, is created in a vector carrying the PAL gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into PAL-encoding sequences is described in Nelson and Long, Analytical Biochemistry 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into the plasmid.

Expression of PAL Variants

According to the invention, a mutated PAL-encoding sequence produced by methods described above, or any alternative methods known in the art, may be expressed using an expression vector which typically includes control sequences encoding a promoter, operator, ribosome binding site, translation initiation signal, and, optionally, a repressor gene or various activator genes. To permit secretion of the expressed protein, nucleotides encoding a "signal sequence" may be inserted prior to the PAL-coding sequence. For expression under the direction of control sequences, a target gene to be treated according to the invention is operably linked to the control sequences in the proper reading frame. Promoter sequences that can be incorporated into plasmid vectors, and which can support the transcription of the mutant PAL gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment B. subtilis is transformed by an expression vector carrying the mutated DNA. If expression is to take place in a secreting microorganism such as B. subtilis a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when present.

In a currently preferred method, the PAL or PAL variants may be produced in a yeast host cell expressing a DNA sequence encoding the enzyme. Examples of preferred yeast hosts are Saccharomyces e.g. Saccharomyces cerevisiae or Saccharomyces kluyveri, Schizosaccharomyces, e.g. Schizosaccharomyces pombe, Kluvveromyces, e.g. Kluyveromyces lactis, Pichia, e.g. Pichia pastoris, or Yarrowia, e.g. Yarrowia lipolytica. The PAL may also be produced in Rhodosporidium toruloides from which the gene is preferentially derived.

The DNA sequence encoding PAL may, for instance be isolated as described in GB 2 213 486. As the amino acid sequence of PAL is known, it may also be possible to construct a synthetic gene encoding the enzyme.

The intracellular expression of PAL may be achieved by linking the PAL-encoding DNA sequence to a suitable control system such as a promoter, ribosome-binding sequences and terminator sequence. Suitable promoters for use in yeast host cells include promoters from yeast glycolytic genes (Hitzeman et al., J. Biol. Chem. 255, 1980, pp. 12073–12080; Alber and Kawasaki, J. Mol. Appl. Gen. 1, 1982, pp. 419–434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304, 1983, pp. 652–654) promoters.

The procedures used to ligate the DNA sequences coding for the PAL, the promoter and the terminator, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

To provide extracellular production of PAL into the culture medium, the control system may include a suitable signal sequence, such as the MFα signal/leader sequence (Kurjan and Herskowitz, Cell, 1982, pp. 933–943). Examples of other signal/leader sequences are described in WO 89/02463 and WO 92/11378.

Transformation of the yeast cells with a vector containing the PAL gene and expression thereof may be carried out according to well-known procedures, e.g. as described in WO 90/10075.

In another method of producing PAL or PAL variants of the invention, a filamentous fungus is used as the host organism. The filamentous fungus host organism may conveniently be one which has previously been used as a host for producing recombinant proteins, e.g. a strain of Aspercillus sp., such as A. niger, A. nidulans or A. oryzae. The use of A. oryzae in the production of recombinant proteins is extensively described in, e.g. EP 238 023.

For expression of PAL variants in Asperaillus, the DNA sequence coding for the PAL variant is preceded by a promoter. The promoter may be any DNA sequence exhibiting a strong transcriptional activity in Asperaillus and may be derived from a gene encoding an extracellular or intracellular protein such as an amylase, a glucoamylase, a protease, a lipase or a glycolytic enzyme.

Examples of suitable promoters are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease or A. oryzae triose phosphate isomerase.

In particular when the host organism is A. oryzae, a preferred promoter for use in the process of the present invention is the A. oryzae TAKA amylase promoter as it exhibits a strong transcriptional activity in A. oryzae. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the PAL variant from the host cell, the DNA sequence encoding the PAL variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral α-amylase, *A. niger* acid-stable α-amylase or *A. niger* glucoamylase.

The medium used to culture the transformed host cells may be any conventional medium suitable for growing Asperaillus cells. The transformants are usually stable and may be cultured in the absence of selection pressure. However, if the transformants are found to be unstable, a selection marker introduced into the cells may be used for selection.

The mature PAL protein may conveniently be recovered from the culture by well-known procedures including lysing the cells and precipitating proteinaceous components of the medium by means of a salt such as ammonium sulphate, followed by chromatographic procedures such as ion exchange chromatography, affinity chromatography, or the like.

The present invention also relates to a pharmaceutical composition containing the enzyme preparation or PAL variant of the invention together with a pharmaceutically acceptable carrier or excipient. In the composition of the invention, the enzyme may be formulated by any one of the established methods of formulating pharmaceutical compositions, e.g. as described in *Remington's Pharmaceutical Sciences*, 1985. The composition should be in a form adapted for oral administration, including a powder, granulate, tablet, capsules, microcapsule, solution or suspension. Suitable carriers and excipients for oral administration are well known in the art.

The pharmaceutical composition of the invention is suitably provided in unit dosage form such as a tablet or capsule. To protect the enzyme from degradation by gastric fluid, such tablets or capsules are preferably provided with an enteric coating, that is, a coating which is insoluble at gastric pH but dissolves at intestinal pH (typically at a pH of 5 or more). Examples of suitable enteric coating agents are cellulose acetate phthalate (CAP, Cellacephate®), vinyl acetate crotonic acid copolymer (Luviset®), methacrylic acid, (meth)acrylic acid ester copolymer (Eudragit®) or hydroxypropyl methylcellulose phthalate. For a further description of enteric coatings and coating processes, reference is made to WO 87/07292. Another suitable pharmaceutical composition is a controlled release formulation from which the enzyme is released during its passage through the gastrointestinal tract.

The composition of the invention may be used for the prevention or treatment of hyperphenylalaninemia, in particular phenylketonuria, as previously suggested by i.a. J. A. Hoskins et al., *Lancet*, Feb. 23, 1980, pp. 392–394; H. J. Gilbert and M. Tully, *Biochem. Biophys. Res. Comm.* 131(2), 1985, pp. 557–563; and L. Bourget and T. M. S. Chang, *Biochim. Biophys. Acta* 883, 1986, pp. 432–438. A suitable dose of PAL to keep the plasma phenylalanine level below the critical level is in the range of from about 50 to about 500 mg PAL protein per day, in particular about 200 mg PAL protein per day.

The invention is described in further detail in the following examples which are not in any way intended to limit the scope of the invention as claimed.

Example 1
Cultivation of PAL Producing Cells

Four strains: *Rhodotorula craminis* (ATCC 20804), *Rhodotorula minuta* (NRRL Y-1589), *Rhodosporidium toruloides* (NRRL Y-1091), and *Rhodotorula aurantiaca* (NRRL Y-7219) were cultured in shake flasks at the following conditions:

Medium: 2% yeast extract, 2% peptone, 0.4% phenylalanine, and 6% glucose

Culture: 26° C., 250 rpm, 4 days

PAL activity was analysed on supernatants after homogenization of culture broth with 1 g of glass beads pr. ml.

Permeabilisation and Immobilisation of Cells by Glutaraldehyde Modification

Cells were diluted with water to reduce viscosity and adjusted to pH 8. They were then frozen at −20° C. in ethanol/dry ice and thawed for permeabilisation. During ice bath cooling, glutaraldehyde was added to a final concentration of 0.5%. pH was readjusted to 8 and stirring continued for 1 hour. The cells were centrifuged for 10 minutes at 7000 rpm. This was repeated after decantation and suspension in 20 ml water followed by freeze-drying of the cells. Details regarding the three cell batches are given below:

| Strain/batch | ATCC 20804 | NRRL Y-1589 | ATCC 20804 |
| --- | --- | --- | --- |
| Cell activity | — | — | 6.6 U/ml* |
| Cell volume used | 11 ml | 16 ml | 9.3 g |
| Added water | 9 ml | 2 ml | 8.2 g |
| pH | 5.6 | 6.2 | 5.7 |
| 4N NaOH → pH 8 | 400 µl | 400 µl | 200 µl |
| Glutaraldehyde, 50% | 200 µl | 180 µl | 177 µl |
| Immobilized PAL | 1.13 g | 2.15 g | 0.94 g |
| Activity | 0.57 U/g | 1.96 U/g | 11.3 U/g |

(#) Immobilization: 2 hours at room temperature. Vacuum drying overnight at 40° C. Ground in mortar.
(*) Approx. activity based on concentrated culture broth.

Comparison Preparations

Acetone permeabilised cells were made basically as described by Gilbert and Tully. The cells were diluted with water and adjusted to pH 8 as for the glutaraldehyde treated cells. They were then added dropwise to 20 volumes of −10° C. acetone (made with dry ice). After standing 15 minutes under occasional stirring, they were allowed to settle for 5–10 minutes. After filtering and re-suspension in 200 ml cold water, cells were collected by centrifugation, 7000 rpm for 12 minutes, followed by freeze-drying. Details for the two batches are given below:

| Strain/batch | NRRL Y-1091 | NRRL Y-7219 |
| --- | --- | --- |
| Cell volume used | 13 ml | 18 ml |
| Added water | 8 ml | 7 ml |
| pH | 7.2 | 7.7 |
| 4N NaOH → pH 8 | 100 µl | 100 µl |
| Acetone | 200 ml | 240 ml |
| Dry cell yield | 0.32 g | 0.44 g |
| Activity | 1.23 U/g | 1.79 U/g |

Activity and Stability Analyses

PAL activity was determined in principle by the measurement of cinnamate at 290 nm from 13 mM phenylalanine, 0.1M Tris, pH 8.5, 37° C. described by Gilbert and Jack. A linear relation between cinnamate concentration and $OD_{290}$ allows calculation of PAL activity in units of µmoles cinnamate/-minute. In order to assay the immobilized preparations, incubation of samples was followed by separation of immobilized PAL before measurement at 290 nm.

Stability towards chymotrypsin with subsequent assay of residual PAL activity was analyzed as follows:

Chymotrypsin (Novo Nordisk, 1000 USP/mg, <25 USP/mg trypsin) was added to the 13 mM phenylalanine substrate (0.1M Tris, pH 8.5) in concentrations of 0, 3, 30, and 300 USP/ml. 25 mg immobilized PAL was added to 10 ml substrate, preheated to 37° C., and shaken at 37° C. (vertically in 20 ml glass tubes). 3.0 ml samples were taken at 5 and 30 minutes and filtered before $OD_{290}$ measurement. Reference: Substrate with chlymotrypsin. Blank samples: Tris-buffer without phenylalanine, with chymotrypsin, and with immobilized PAL. Reference to blank samples: Chymotrypsin in Tris-buffer.

Activity calculation:

Activity in $U/g = \epsilon * l * v * [(E_{30} - E_{30B}) - (E_5 - E_{5B})]/t*m$ $\epsilon$=molar extinction coefficient of cinnamate: $1*10^4$ liter/-mole/cm l=cuvette width: 1 cm V=substrate volume: 10 ml t=reaction time: 25 minutes m=amount of enzyme: 25 mg $E_{30}$=extinction of sample at 30 minutes $E_{30B}$=extinction of blank at 30 minutes $E_5$=extinction of sample at 5 minutes $E_{5B}$=extinction of blank at 5 minutes With these values, $A=1.60 * [(E_{30}-E_{30B})-(E_5-E_{5B})]$, in U/g Soluble PAL (Sigma P-1016, lot 22H8000, from Rhodotorula glutinis) was analysed to 2.8 U/ml and diluted 1:10 prior to incubation with 2.6 USP/ml chymotrypsin (batch as above) in 0.1M Tris, pH 7.5, 370° C. Residual PAL activity was assayed after 15 and 30 minutes and calculated relative to original activity.

Results:

| Immobilized preparation | Residual activity, U/g and %, at different chymotrypsin levels | | | |
|---|---|---|---|---|
| | 0 USP/ml | 3 USP/ml | 30 USP/ml | 300 USP/ml |
| Glutaraldehyde treated ATCC 20804100 | 0.57 100 | 0.53 93 | 0.53 93 | 0.44 77 |
| Glutaraldehyde treated NRRL Y-1589 | 1.96 100 | 1.69 86 | 1.76 90 | 1.34 68 |
| Glutaraldehyde treated ATCC 20804 | 11.3 100 | — — | — — | 11.3 100 |
| Comparisons preparations | | | | |
| Acetone permeabilized NRR1 Y-1091 | 1.23 100 | 0.89 72 | 0.55 45 | 0.28 23 |
| Acetone permeabilized NRRL Y-7219 | 1.79 100 | 1.11 62 | 0.90 50 | 0.54 30 |
| Soluble PAL | 2.8 U/ml 100% | 0.02 U/ml 0.8% (2.5% after 15 minutes) | | |

These results demonstrate the efficiency of glutaraldehyde treatment in stabilizing PAL-containing Rhodotorula cells towards chymotrypsin.

We claim:

1. An enzyme preparation comprising phenylalanine ammonia lyase (PAL) stabilised against proteolytic degradation by treatment with a cross-linking agent which is a bifunctional reagent or in which one or more amino acid residues susceptible to proteolytic cleavage are replaced by other amino acid residues less susceptible to proteolytic cleavage.

2. The enzyme preparation according to claim 1 which includes whole cells containing PAL, permeabilised cells containing PAL, a cell homogenate containing PAL or cell-free PAL.

3. The enzyme preparation according to claim 1, in which PAL constitutes at least 25% of the enzyme protein in the preparation.

4. The enzyme preparation according to claim 1, in which PAL constitutes at least 50% of the enzyme protein in the preparation.

5. The enzyme preparation according to claim 1, wherein the PAL is in crystalline form.

6. The enzyme preparation according to claim 1, wherein the cross-linking agent is selected from the group consisting of pharmaceutically acceptable carbodiimides, isoxazolium derivatives, chloroformates, carbonyldiimidazole, bis-imidoesters, bis-succinimidyl derivatives, di-isocyanates, di-isothiocyanates, di-sylfonyl halides, bis-nitrophenyl esters, dialdehydes, diacylazides, bis-maleimides, bis-haloacetyl derivatives, di-alkyl halides and bis-oxiranes.

7. The enzyme preparation according to claim 4, wherein the dialdehyde is glutaraldehyde.

8. The enzyme preparation according to claim 1, wherein the PAL is derivable from a microorganism.

9. The enzyme preparation according to claim 1, wherein the PAL is derivable from a fungus.

10. The enzyme preparation according to claim 1, wherein the PAL is derivable from a fungus selected from the group consisting of Rhodotorula sp., Rhodosporidium sp., Sporobolus sp., Geotrichum sp., Moniliella sp., Pellicularia sp, Gonatobotryum sp., Syncephalastrum sp., Endomyces sp., Aspergillus sp., Saccharomycopsis sp., Eurotium sp., Glomerella sp., Cladosporium sp. and Trichosporon sp.

11. The enzyme preparation according to claim 1, wherein the PAL is derivable from a plant.

12. The enzyme preparation according to claim 1, wherein the PAL is derivable from a plant selected from the group consisting of Pisum sativum, potato, sweet potato and soy bean.

13. A PAL variant stabilised against proteolytic degradation, wherein one or more amino acid residues susceptible to proteolytic cleavage are replaced by other amino acid residues less susceptible to proteolytic cleavage.

14. The PAL variant according to claim 13, wherein one or more of the amino acid residues Phe, Tyr, Trp, Lys or Arg are replaced by other amino acid residues.

15. The PAL variant according to claim 13, wherein the parental PAL is derived from a microorganism.

16. The PAL variant according to claim 13, wherein the parental PAL is derived from a fungus.

17. The PAL variant according to claim 13, wherein the parental PAL is derived from a fungus selected from the group consisting of Rhodotorula sp., Rhodosporidium sp., Sporobolus sp., Geotrichum sp., Moniliella sp., Pellicularia sp, Gonatobotryum sp., Syncephalastrum sp., Endomyces sp., Aspergillus sp., Saccharomycopsis sp., Eurotium sp., Glomerella sp., Cladosporium sp. and Trichosporon sp.

18. The PAL variant according to claim 13, wherein the parental PAL is derived from a plant.

19. The PAL variant according to claim 13, wherein the parental PAL is derived from a plant selected from the group consisting of Pisum sativum, potato, sweet potato and soy bean.

20. The PAL variant according to claim 13, wherein the parental PAL is derived from *Rhodosporidium toruloides*.

21. The PAL variant according to claim 20, wherein one or more amino acid residues are substituted in the region from amino acid 629 to 674.

22. The PAL variant according to claim 21, wherein one or more amino acid residues are substituted as follows

F629A,S,V,L,E,P,N,I,Q,T,M,G,H,D

F631 A,S,V,L,E,P,N,I,Q,T,M,G,H,D

W653A,S,V,L,E,P,N,I,Q,T,M,G,H,D

K654A,S,V,L,E,P,N,I,Q,T,M,G,H,D

R667A,S,V,L,E,P,N,I,Q,T,M,G,H,D

R670A,S,V,L,E,P,N,I,Q,T,M,G,H,D

F673A,S,V,L,E,P,N,I,Q,T,M,G,H,D

W674A,S,V,L,E,P,N,I,Q,T,M,G,H,D.

23. A DNA construct comprising a DNA sequence encoding the PAL variant according to claim 13.

24. A recombinant expression vector comprising a DNA construct according to claim 23.

25. A cell transformed with a DNA construct according to claim 23.

26. The cell according to claim 25, in which the cell is a microbial cell.

27. The cell according to claim 25, in which the cell is a yeast cell.

28. The cell according to claim 25, in which the cell is a yeast cell selected from the group consisting of *Rhodotorula glutinis*, Saccharomyces, Schizosaccharomyces, Kluyveromyces, Pichia, and Yarrowia.

29. The cell according to claim 25, in which the cell is a *Saccharomyces cerevisiae* or *Saccharomyces kluyveri cell*.

30. The cell according to claim 25, in which the cell is a *Kluyveromyces lactis cell*.

31. The cell according to claim 25, in which the cell is a *Yarrowia lipolytica* cell.

32. The cell according to claim 23, in which the cell is a *Schizosaccharomyces pombe* cell.

33. The cell according to claim 25, in which the cell is a *Pichia pastoris* cell.

34. The cell according to claim 25, in which the cell is a filamentous fungal cell.

35. The cell according to claim 25, in which the cell is a filamentous fungal cell selected from the group consisting of Aspergillus and Trichoderma.

36. The cell according to claim 25, in which the cell is selected from the group consisting of *Aspergillus niger*, *Aspergillus oryzae* and *Aspergillus nidulans*.

37. The cell according to claim 25, in which the cell is a *Trichoderma reseei* cell.

38. A process for preparing a PAL variant according to claim 13, comprising culturing a cell transformed with a DNA construct comprising a DNA sequence encoding the PAL variant in a suitable culture medium under conditions permitting production of the PAL variant, and recovering the resulting PAL variant from the culture.

39. A pharmaceutical composition adapted for oral administration comprising an enzyme preparation according to claim 1 together with a pharmaceutically acceptable carrier or excipient.

40. A pharmaceutical composition for the prevention or treatment of hyperphenylalaninemia comprising an enzyme preparation according to claim 1 together with a pharmaceutically acceptable carrier or excipient.

41. A composition according to claim 40 in the form of a tablet or capsule provided with an enteric coating.

42. A pharmaceutical composition adapted for oral administration comprising a PAL variant according to claim 13 together with a pharmaceutically acceptable carrier or excipient.

43. A pharmaceutical composition for the prevention or treatment of hyperphenylalaninemia comprising a PAL variant according to claim 13 together with a pharmaceutically acceptable carrier or excipient.

44. A composition according to claim 42 in the form of a tablet or capsule provided with an enteric coating.

\* \* \* \* \*